United States Patent
Obrien et al.

(10) Patent No.: US 9,690,974 B2
(45) Date of Patent: Jun. 27, 2017

(54) OPTICAL PLATELET COUNTER METHOD

(71) Applicant: FOCE Technology International BV, Maria Hoop (NL)

(72) Inventors: Thomas Obrien, Eindhoven (NL); Hendrik Dijkstra, Eindhoven (NL); Marcel F Schemmann, Maria Hoop (NL)

(73) Assignee: 2M Engineering Limited (NL)

( * ) Notice: Subject to any disclaimer, the term of this patent is extended or adjusted under 35 U.S.C. 154(b) by 0 days.

(21) Appl. No.: 14/223,784

(22) Filed: Mar. 24, 2014

(65) Prior Publication Data

US 2014/0205176 A1 Jul. 24, 2014

Related U.S. Application Data (63) Continuation of application No. PCT/IB2012/001857, filed on Sep. 24, 2012.

(60) Provisional application No. 61/537,625, filed on Sep. 22, 2011.

(51) Int. Cl.
| | |
|---|---|
| G06K 9/00 | (2006.01) |
| G02B 21/36 | (2006.01) |
| G01N 15/14 | (2006.01) |
| G01N 15/00 | (2006.01) |

(52) U.S. Cl.
CPC ..... G06K 9/00134 (2013.01); G01N 15/1434 (2013.01); G01N 15/1475 (2013.01); G02B 21/365 (2013.01); G01N 2015/0065 (2013.01); G01N 2015/1445 (2013.01)

(58) Field of Classification Search
None
See application file for complete search history.

(56) References Cited

U.S. PATENT DOCUMENTS

| | | | |
|---|---|---|---|
| 6,473,228 B1 * | 10/2002 | Toshimitsu | 359/368 |
| 2003/0227673 A1 | 12/2003 | Nakagawa | |
| 2004/0241677 A1 | 12/2004 | Lin et al. | |
| 2008/0019584 A1 | 1/2008 | Lindberg et al. | |

(Continued)

OTHER PUBLICATIONS

Wayback Machine Engine, https://web.archive.org/web/20090309125200/http://www.wadsworth.org/chemheme/heme/microscope/celllist.htm Wadsworth Center of New York, Dec. 2008-Mar. 2009.*

(Continued)

*Primary Examiner* — Stephen R Koziol
*Assistant Examiner* — Pinalben Patel
(74) *Attorney, Agent, or Firm* — FSP LLC (57) ABSTRACT

Platelets or blood cells are detected in a fluid sample by adjusting a focal depth of a microscope through a range of values, the microscope having a mounted sample and an objective lens adapted with one or both of (a) a spherical aberration correction unmatched to a utilized cover plate for the sample, or (2) a numerical aperture unmatched to a utilized illumination source for the sample. Images are recorded at different specific focal depths and in multiple z planes of a fluid bearing the platelets, where the position of platelets may overlap on different of the multiple z planes that are recorded, the images recorded through the cover plate, thus causing the generation of a specific light-dark pattern indicative of platelets at particular positions and at multiple depths in the fluid media. The images are analyzed for the specific light-dark pattern.

11 Claims, 5 Drawing Sheets

(56) References Cited

U.S. PATENT DOCUMENTS

| | | | |
|---|---|---|---|
| 2008/0158666 A1* | 7/2008 | Seale | G02B 21/04 |
| | | | 359/368 |
| 2009/0185714 A1* | 7/2009 | Lindberg et al. | 382/100 |
| 2010/0213063 A1* | 8/2010 | Zenhausern et al. | 204/452 |
| 2010/0232674 A1* | 9/2010 | Amakawa | G06K 9/00134 |
| | | | 382/133 |
| 2011/0134233 A1 | 6/2011 | Alexandrov | |
| 2011/0254943 A1* | 10/2011 | Ozinsky | G06K 9/00134 |
| | | | 348/79 |

OTHER PUBLICATIONS

Ghosh, Statistical Pattern Analysis of White Blood Cell Nuclei Morphometry, Proceedings of 2010 IEEE students technologies symposium, Apr. 3-4, 2010, IIT Kharagpur.*

International Preliminary Report on Patentability for application No. PCT/IB2012/001857, mailed Mar. 25, 2014.

* cited by examiner

OPTICAL PLATELET COUNTER METHOD

TECHNICAL FIELD

The invention is generally in the field of quantification of particles via microscopy.

BACKGROUND

Blood platelet analysis and quantification play an important role in many medical treatments. A microscope is typically used to take a picture of a fluid layer containing platelets. The fluid is sometimes covered by a transparent plate, usually a thin sheet of glass. In some applications no cover plate is used.

Analysis is performed to detect round shapes within a size range associated with platelets. Platelets appear dark in the image, This pattern is identified against a background of other objects such as red blood cell remnants and dust particles. The microscope focus is precisely determined in order to image the platelets as described above. The microscope objective lens is adapted to account for imperfect spherical aberration of the lens, and to account for the optical distortion produced the cover plate that covers the sample (if there is a cover plate at all).

White blood cells are cells found in the blood that form part of the body's defenses against foreign bodies. They are larger than platelets and red blood cells. There are 5 types of white blood cells of interest differ in size and shape. Altogether, there are approx. 7×109/liter white blood cells in blood.

Neutrophil granulocyte is the most common white blood cell to be found in the human blood (62%). They have a spherical shape when inactivated with a diameter of 10-12 μm and a segmented nucleus.

The Eosinophil granulocyte is less common (2.3%) and will be transparent if not dyed. Its shape is very similar to the neutrophil with its diameter also being around 10-12 μm. Eosinophils together with neutrophils and basophils are granulocytes meaning they have big granules their cytoplasm.

Basophil granulocyte is a white blood cell that is even less common (0.4%). As the name states it is very easily stained. If the cell is not dyed it will appear partly transparent as it is only the nucleus that is clearly visible.

Large granular lymphocytes have a diameter between 12-15 μm. The cell's nucleus occupies most of the cell and is clearly visible. The small granular Lymphocyte has the same shape however a diameter which is smaller (7-8 μm). The percentage of this white blood cell being in an adult's blood is approx. 30%.

Monocytes have a cell diameter between 7.72-9.99 μm and account for approx. 5% of the white blood cells in humans. Monocytes are very diverse in shape and thus can be easily confused for other cells. They can be recognized by their non-circular multi-, di-, tri-lobed nucleus.

Red blood cells are the most abundant cells in the blood stream. They have a disk diameter of approximately 6.2-8.2 μm and a thickness at the thickest point of 2-2.5 μm, with a minimum thickness in the center of 0.8-1 μm. They are bi concave in shape and a normal concentration for humans is approx. 5×106/μl.

The conventional microscopy approach to counting white blood cells and red blood cells in a sample is similar in many respects.

DISCLOSURE OF THE INVENTION

Figure 4:
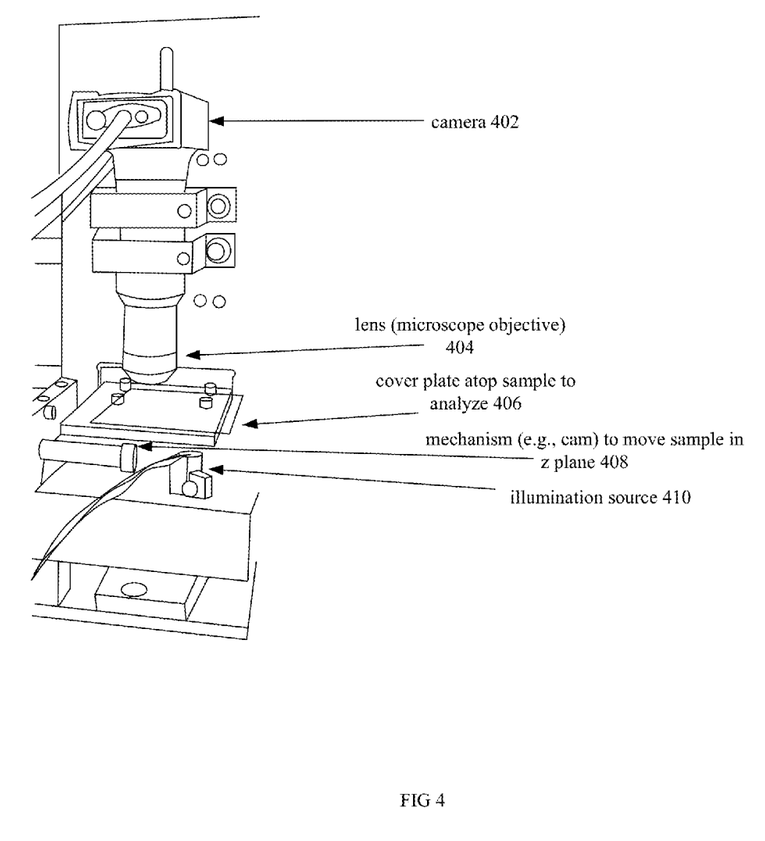
FIG. 4 illustrates an example of a microscope arrangement to facilitate the procedures described herein.

The focus of a microscope is varied through a range of values, and images of a platelet medium are recorded through a covering plate that is thicker than a plate thickness setting for which the microscope objective has been corrected. The covering plate is typically plastic or glass and is deliberately thicker than the plate thickness for which the microscope objective is corrected. Multiple images are taken at different focal depths. Platelets (or other type cells) are detected throughout a range of a liquid sample depth, not just on a settling surface or single plane. An example microscope arrangement is illustrated in FIG. 4.

Figure 5:
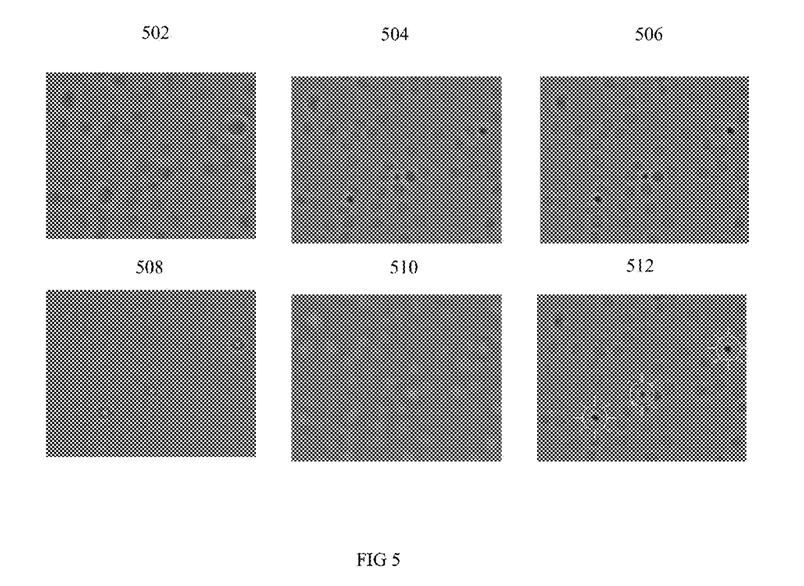
FIG. 5 illustrates an example of an evolving optical pattern for detecting platelets in blood as described herein.

- 402 camera
- 404 lens (microscope objective)
- 406 cover plate atop sample to analyze
- 408 mechanism (e.g., cam) to move sample in z plane
- 410 illumination source The plate thickness, and also possibly the plate material, and selected in relation to the microscope objective correction to deliberately cause the generation of a particular optical pattern as the focus depth is changed. This pattern is exemplified as follows (for increasing focal depth—the reverse is generated for progressively decreasing focal depth): platelets will appear as blurry dark spots that focus into sharp small dark spots 1-6 um in size as the focal depth is progressively increased. Continuing to progressively increase the focal depth will cause the small dark spots to evolve into bright spots with a small dark edge that then increases in size, and blurs out. FIG. 5 shows examples of an evolving optical pattern that may be generated, including examples of "dark", "spots", "blurry", "sharp", and a "small dark edge".

- 502 above focus (blurry black)
- 504 approaching focus (sharper)
- 506 focus (sharp black)
- 508 through focus (white dots with black ring)
- 510 further through focus (white blurry)
- 512 detected platelets marked with circles.

Generation and recording of a particular optical pattern indicative of the presence of platelets is thus accomplished, via progression of the focus depth through a preselected range, and due to particular selection of a covering plate thickness (and optionally material) relative to the correction applied to the microscope, to cause said pattern to be generated. The recorded pattern may then be analyzed to quantify/qualify the presence of platelets. Alternatively, analysis may be undertaken during image acquisition at the different focal depths, instead of waiting until all images are acquired.

In some embodiments, a deliberate choice of a covering plate thickness that does not match the microscope objective is made; in other embodiments, it is not required to deliberately mismatch the objective and cover plate. A lower cost, lower quality microscope objectives with poor spherical aberration may be employed with a matching cover plate, and/or a wide viewing field, causing poor spherical aberration correction and thus generating the desired optical pattern.

Conventional optical microscopy techniques match the numerical aperture (NA) of the illumination with the NA of the objective lens. In contrast, in the disclosed technique the optical path of the platelet counter contains an illumination with a very low NA: the illumination light beams are (almost) parallel. The sample is, for example, illuminated from below by a parallel or close-to-parallel beam formed by using an illumination source at a large distance (relative to the sample depth), for instance >10 cm.

Under these illumination conditions, images of the platelets (or other cells) in the sample are recorded in focus, and out of focus, both nearer to the objective lens and further away from the objective lens. This results in the bright/dark transitions that are processed in specific ways to detect the specific particles of interest.

Certain desired optical transitions in the set of recorded images may be obtained by deliberate selection of one or both of 91) an insufficient spherical aberration correction in the microscope objective for the covering plate, and (2) a deliberately low NA illumination in relation to the NA of the lens.

BEST MODE AND INDUSTRIAL APPLICABILITY

Preliminaries

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

The term "approximately" refers to a value within 20% of the stated value.

"Logic" refers to machine memory circuits, machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein.

The techniques and procedures described herein may be implemented via logic distributed in one or more computing devices. The particular distribution and choice of logic is a design decision that will vary according to implementation.

Platelets

As the focus of a microscope is varied through a z range under (or over) a sample utilizing a cover plate, the image brightness in the center of a given platelet will first go from neutral dark, then go bright and then return back to dark (or reverse of this if the focal depth is progressively decreased). A characteristic pattern will result that is a function of focal depth. Correlation analysis may be performed to reject a major part of the background noise, while detecting the pattern. During transition of the microscope through a range of focus depths, as described above, background features not indicative of platelets may not vary as much with changes in the focal depth as do platelet features. These background features include dust in the optical system and on the camera lens.

Correlations may be determined that provide individual peak results at various focal depths. Even when the exact focal depth is unknown, the correlation analysis over multiple depths may nonetheless result in a correct analysis and quantification/qualification of platelets in the sample.

The described technique may thus yield an improved discrimination against unwanted signals over conventional methods (see Background). Furthermore, the described technique enables the use of lower cost cover plates and lower cost microscope objectives.

Figure 1:
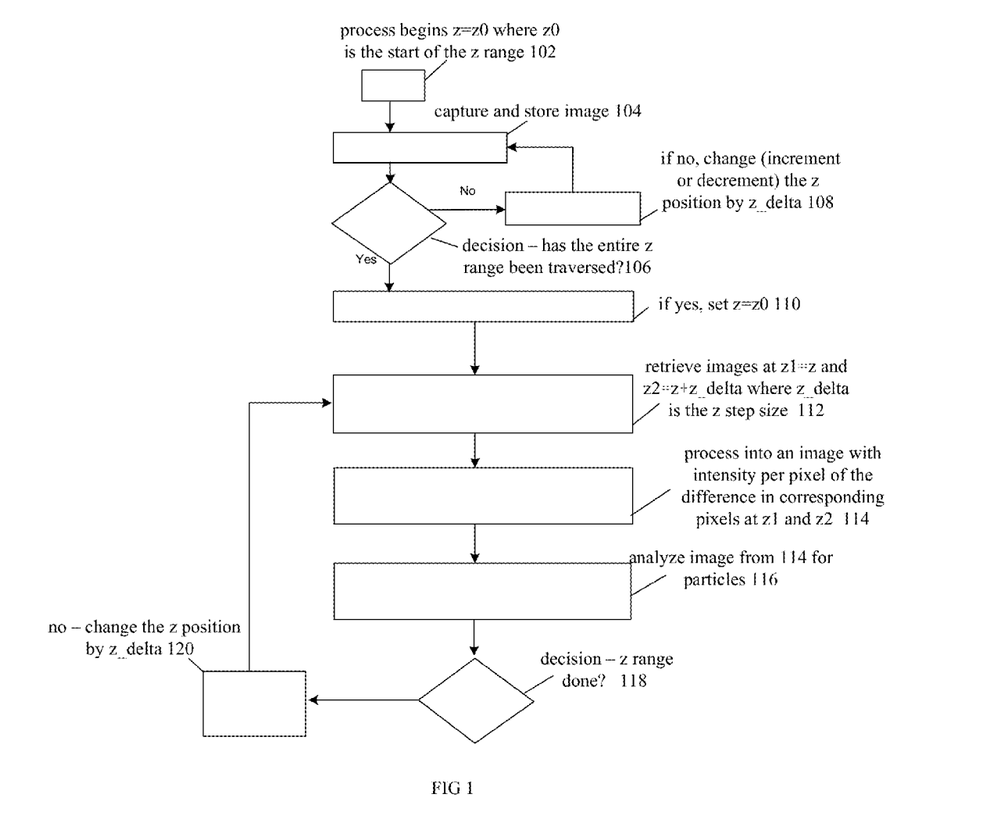
FIG. 1 illustrates an embodiment of a process to analyze for platelets in a fixed (very low fluid dynamic) fluid sample.

Discrimination analysis may begin with collection of a number of images at different Z (focus) positions throughout a range. An intensity difference is determined between images separated by a distance z_delta where z_delta is the distance difference for which typically a large black/white contrast is expected for the pictures. For each image pair separated by z_delta, the processed image with the intensity difference is used to determine the number of platelet particles in the image, and to record their locations. An embodiment of this process, which may be carried out, for example, in logic coupled with the microscope, is illustrated in FIG. 1.

102 process begins $z=z0$ where $z0$ is the start of the z range 104 capture and store image 106 decision—has the entire z range been traversed?

108 if no, change (increment or decrement) the z position by z_delta 110 if yes, set $z=z0$ 112 retrieve images at $z1=z$ and $z2=z+z\_delta$ where z_delta is the z step size 114 process into an image with intensity per pixel of the difference in corresponding pixels at $z1$ and $z2$ 116 analyze image from 114 for particles 118 decision—z range done?

120 no—change the z position by z_delta

The detection of platelets in an image may for instance be implemented based on template recognition as available in many image analysis products. In the difference picture a platelet may for instance have a shape that is bright in the center and has a dark edge. This shape is incorporated into the template recognition algorithm. Alternately the template recognition logic is input a known positive result of a platelet and compares a set of positions in the image with this known positive result. Applying the difference operation enhances the signature of particles to be detected while at the same time suppressing most other unwanted artifacts such as dust in the microscope or larger structures that affect the intensity distribution in the image.

Figure 2:
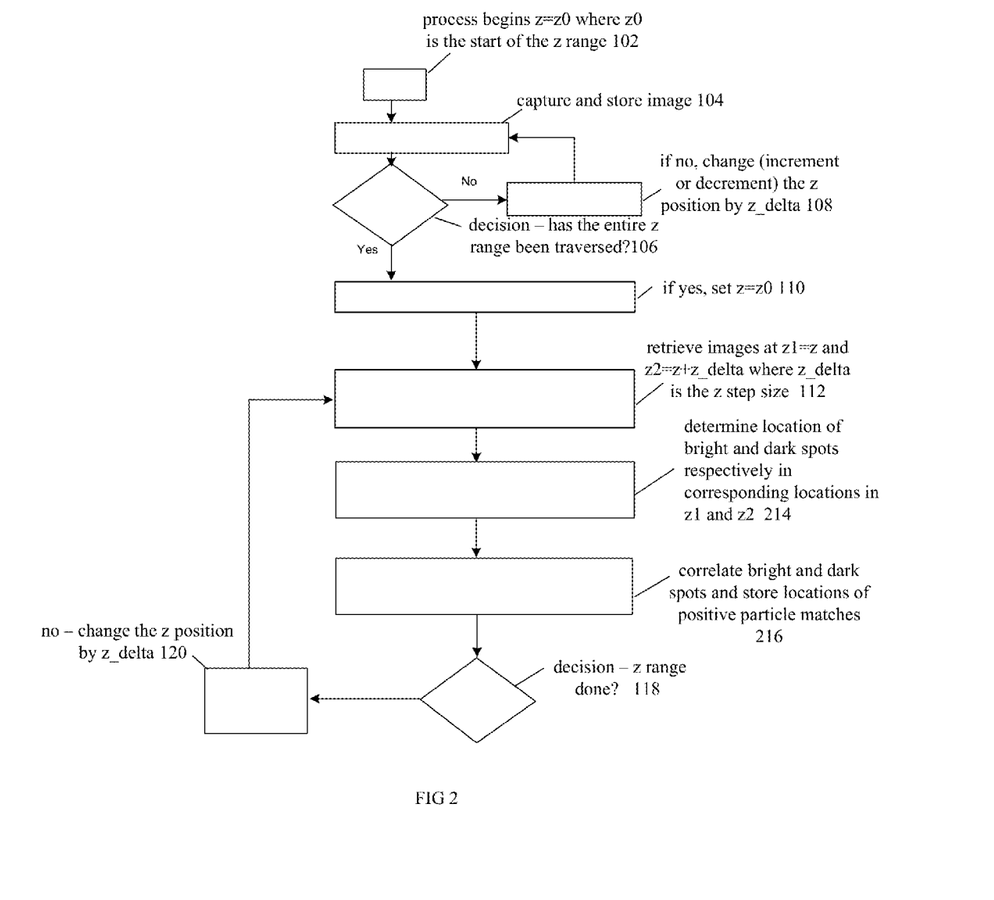
FIG. 2 illustrates an embodiment of a process to analyze for platelets in a moving (fluid dynamics within an acceptable range) fluid sample.

The difference operation may be implemented as an anti-correlation. Platelets will manifest as bright spots at one z location (focus) and dark at another. The location of bright spots and dark spots may then be correlated at different z positions. Template recognition may be employed both for bright spots and dark spots at each one of the images recorded at each Z position. This results in a number of bright and dark spot positions in each image. These positions are correlated such that for each dark spot at a location for focus z, a bright spot at focus z+z_delta must be identified at that same location. Doing so confirms the anti-correlation of image intensity at that location between focus z and focus z_z_delta. This greatly suppresses false detection due to artifacts. FIG. 2 illustrates an example of this process.

102 process begins z=z0 where z0 is the start of the z range 104 capture and store image 106 decision—has the entire z range been traversed?

108 if no, change (increment or decrement) the z position by z_delta 110 if yes, set z=z0

112 retrieve images at z1=z and z2=z+z_delta where z_delta is the z step size 214 determine location of bright and dark spots respectively in corresponding locations in z1 and z2

216 correlate bright and dark spots and store locations of positive particle matches 118 decision—z range done?

120 no—change the z position by z_delta

This process described in conjunction with FIG. 2 may handle platelet displacements due to moving platelet fluid medium while the microscope is stepped through its z (focus) range to record the images. Fluid displacement may cause the exact location of correlated dark and bright spots at different focus positions to differ at the time the images at the different microscope focus depths are recorded. Assume dark spots have been identified, and associated bright spots must now be identified at a different focal depth to determine that the spots correspond to platelets. A defined area around the original dark spot may be analyzed, which accounts for a predictable amount of fluid displacement.

The technique described in conjunction with FIG. 1 relies on image intensity difference calculation, so that a small platelet displacement on the order of magnitude of the platelet dimensions themselves will render the difference picture less useful or useless for analysis. Thus this technique may be best applied after the fluid medium for the particles has settled or has been fixed. However the technique described in conjunction with FIG. 2 tolerates limited fluid motion and may for instance be applied even before a fluid has not fully settled.

Figure 3:
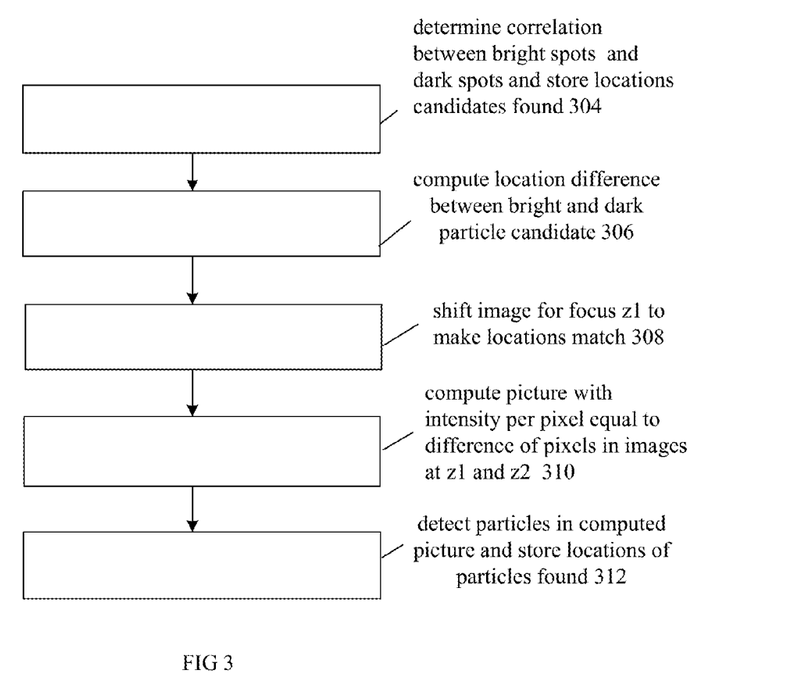
FIG. 3 illustrates an embodiment of a process combining aspects of the processes illustrated in FIGS. 1 & 2.

The methods described in conjunction with FIGS. 1 and 2 may be combined. The correlation between bright spots and dark spots may determine platelet candidate locations. These candidates are likely true platelets but may also include false detections. A location difference is determined between the originating bright and dark spots in their images at the two different z locations. The two images (or at least the part of the images that contains the candidate) are shifted such that the bright spot and the dark spots overlap. A difference image is generated and on the difference image a template match is undertaken. The difference image enhances wanted particle information and suppresses unwanted artifacts, simplifying the detection of platelets. FIG. 3 illustrates an example of this combined process (e.g., action 216 of FIG. 2).

304 determine correlation between bright spots and dark spots and store locations candidates found 306 compute location difference between bright and dark particle candidate 308 shift image for focus z1 to make locations match 310 compute picture with intensity per pixel equal to difference of pixels in images at z1 and z2

312 detect particles in computed picture and store locations of particles found

In one implementation, the slides are 100 micrometers deep while the z range is 320 micrometers. Another example implementation uses a z range of 1 to 2 mm Three frames per second are collected, making the time between frames 0.333 seconds. The z delta is 8 micrometers resulting in 40 frames collected. Another example uses a z delta of 6 micrometers.

In one advantageous mode, the illumination source is a blue LED source (wavelength 470 nm) placed at a distance of around 140 mm under a liquid sample (conventional liquid media for such samples) with platelets. No condenser lens is deployed between the LED and the liquid.

The specimen of liquid with platelets may be contained by an approximately 100 micrometer high chamber between a transparent plastic ground plate and a transparent plastic covering plate. An Olympus Plan N 10×/0.25 ∞/–/FN22 UIS 2 objective lens is utilized with no correction value for "cover glass thickness". Spherical aberration is thus introduced for any cover plate thickness. A glass ground plate and a glass covering plate may also be used, or a combination of plastic and ground plates.

Approximately 40 images may be taken at different z depths in the sample, at a rate of three images per second. As a starting point, the objective lens is focused at 100 micrometers above the sample chamber. For each next image, the focus of the objective lens is lowered 8 micrometers. The last image is focused 112 micrometers below the sample chamber. The z range for image acquisition is thus 100 um (above chamber)+100 um (chamber height)+112 (below chamber), for about 312 um of total range.

For detecting platelets near the top of the chamber images that focus above the chamber may be used. Platelets at the top are stuck to the upper (glass or plastic) window. For detecting platelets near the bottom of the chamber images that focus below the chamber may be used. Platelets at the bottom are stuck to the bottom surface. This is typically the only plane at which conventional approaches detect the platelets.

In an image where the objective lens focuses above the object, the object must match with a first template to be a candidate for a positive match to a platelet. This template represents the optical appearance of a platelet below the image focal plane: a dark ring around a bright center. Thus at some z position "z_first" an image must be found that matches what is expected for focus above the object.

In an image where the objective lens focuses at or near the object, the object must match with the second template. This template represents the optical appearance of a platelet in or near the focal plane: a dark circular shape. This means at some z position z_second an image must be found that matches what is expected for focus at the object where z_first is larger than z_second.

In an image where the objective lens focuses below the object, the object must match with a third template. This template represents the optical appearance of a platelet below the image plane: white center with dark ring. Thus at some z position z_third an image must be found that matches what is expected for focus below the object were z_third must be larger than z_second.

In the z (vertical) direction, the matches for the first and second templates may be at most nine images apart. In the perpendicular x and y directions, the matches for the first and second templates can be at most seven pixels apart, to compensate for object motion in the x-y plane. Each pixel covers 0.63 micrometers in the x direction and 0.63 micrometers in the y direction (these are all examples that may vary in other implementations). Applying these values, it is possible to compensate for a movement of 0.63*7=4.41 um. in the x direction and in the y direction. Thus in this example the object matches at z_first and z_second must be within 4.41 um in either x or y direction.

The platelet count becomes inaccurate when the motion exceeds a limit. For example, when more than 15% of the matching objects move in the range 2.8 to 4.1 micrometers, the overall count may be adversely affected. Overall (for all detected platelets) no more than 15% may move in the 2.8-4.1 um range, in this example, or else the count may be unreliable.

An increase in the allowed number of pixels between the matches of the first and second templates will increase the probability of an erroneous match between neighboring platelets.

A similar motion compensation may be applied for the object matches in the second and third templates. Thus the image matches at z_second and z_third must be within 4.41 um in either x or y direction.

White Blood Cells

A count of white or red blood cells may be obtained utilizing similar mechanics as for platelets, i.e., similar focus scanning through the same type(s) of slide and similar mismatch of objective aberration correction and slide, or NA and illumination. The "mechanics" means the mechanical implementation and the camera, illumination and microscope objective. The mechanics are similar, but the optical effects and templates are different for white blood cells and red blood cells.

Unlike platelets, where the optical pattern changes over a small number of frames, changes associated with white blood cells require most of the 40 frames to become apparent. Three different optical patterns indicative of white cells may be apparent.

The first pattern has a black ring surrounding a white core. The white core becomes smaller and completely black with a white ring surrounding it as the z position for focus is varies.

The second pattern is similar to the first pattern however it has a more greyish core at first in comparison to the white core in the first pattern. The white ring around the black core is also present.

The third pattern is less visible as it is completely grey circle in the beginning. It then turns into a black circle and finally into a white core surrounded by a grey circle as the focus the z-position is varied.

Red Blood Cells

The red blood cells begin (out of focus) as grey outside ring surrounding a white center. With increasing depth, the center turned grey and the outside ring was a darker grey. They then went to a smaller white center surrounded by a dark grey/black ring. Finally, they turned into a dark grey center surrounded by a large grey outside ring. Again as we change the z-position the above occurs.

Implementations and Alternatives

The techniques and procedures described herein may be implemented via logic distributed in one or more computing devices. The particular distribution and choice of logic is a design decision that will vary according to implementation.

Those having skill in the art will appreciate that there are various logic implementations by which processes and/or systems described herein can be effected (e.g., hardware, software, and/or firmware), and that the preferred vehicle will vary with the context in which the processes are deployed. "Software" refers to logic that may be readily readapted to different purposes (e.g. read/write volatile or nonvolatile memory or media). "Firmware" refers to logic embodied as read-only memories and/or media. Hardware refers to logic embodied as analog and/or digital circuits. If an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations may involve optically-oriented hardware, software, and or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood as notorious by those within the art that each function and/or operation within such block diagrams, flowcharts, or examples can be implemented, individually and/or collectively, by a wide range of hardware, software, firmware, or virtually any combination thereof. Several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory.

In a general sense, those skilled in the art will recognize that the various aspects described herein which can be implemented, individually and/or collectively, by a wide range of hardware, software, firmware, or any combination thereof can be viewed as being composed of various types of "circuitry." Consequently, as used herein "circuitry" includes, but is not limited to, electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), circuitry forming a memory device (e.g., forms of random access memory), and/or circuitry forming a communications device (e.g., a modem, communications switch, or optical-electrical equipment).

Those skilled in the art will recognize that it is common within the art to describe devices and/or processes in the fashion set forth herein, and thereafter use standard engineering practices to integrate such described devices and/or processes into larger systems. That is, at least a portion of the devices and/or processes described herein can be integrated into a network processing system via a reasonable amount of experimentation.

The foregoing described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

What is claimed is:

1. An optical organic particle counting method, comprising:
adjusting a microscope focal depth of a microscope through a range of values of the microscope focal depth, the microscope having a microscope focal arrangement adapted to form a plurality of blurry images of organic particles in a z plane of a fluid sample at different ones of the range of values of the microscope focal depth, wherein the different ones of the range of values of the microscope focal depth comprises at least one focal plane above the z plane of the organic particles and at least one focal plane below the z plane of the organic particles;
recording the plurality of blurry images of the organic particles at the different ones of the range of values of the microscope focal depth, wherein coordinates of the organic particles overlap on the plurality of blurry images, thus causing the generation of a specific light-dark pattern across the plurality of blurry images indicative of the organic particles; and
analyzing the plurality of blurry images for the specific light-dark pattern across the plurality of blurry images to identify and classify the organic particles.

2. The method of claim 1, further comprising:
the range of values of the microscope focal depth being approximately 320 micrometers and a slide depth of approximately 100 micrometers.

3. The method of claim 1, further comprising:
the plurality of blurry images being at least 40 images recorded at three images per second.

4. The method of claim 1, further comprising:
the microscope focal arrangement comprising a blue LED illumination source having a wavelength of approximately 470 nm placed at a distance of approximately 140 mm under the fluid sample.

5. The method of claim 1, further comprising the specific light-dark pattern across the plurality of blurry images comprising, in forward or reverse order:
(a) a dark ring around a bright center;
(b) a dark circular shape; and
(c) a white center with dark ring.

6. The method of claim 1, the specific light-dark pattern across the plurality of blurry images comprising, in forward or reverse order:
(a) a black ring surrounding a white core; and
(b) the white core growing smaller and turning black, with a white ring surrounding it.

7. The method of claim 1, the specific light-dark pattern across the plurality of blurry images comprising, in forward or reverse order:
(a) a black ring surrounding a greyish core; and
(b) the greyish core growing smaller and turning black, with a white ring surrounding it.

8. The method of claim 1, the specific light-dark pattern across the plurality of blurry images comprising, in forward or reverse order:
(a) a grey center and an outside ring of a darker grey;
(b) a smaller white center surrounded by a dark grey or black ring; and
(c) a dark grey center surrounded by a large grey outside ring.

9. The method of claim 1, the specific light-dark pattern across the plurality of blurry images comprising, in forward or reverse order:
(a) a completely grey circle;
(b) a black circle; and
(c) a white core surrounded by a grey circle.

10. The method of claim 1, wherein the organic particles are platelets.

11. The method of claim 1, wherein the organic particles are blood cells.

* * * * *